US00PP07943P

United States Patent [19]

Warriner

[11] Patent Number: Plant 7,943

[45] Date of Patent: Aug. 18, 1992

[54] ROSE PLANT JACFON

[75] Inventor: William A. Warriner, Tustin, Calif.

[73] Assignee: Bear Creek Gardens, Inc., Medford, Oreg.

[21] Appl. No.: 625,912

[22] Filed: Dec. 10, 1990

[51] Int. Cl.[5] ..... A01H 5/00

[52] U.S. Cl. ..... Plt./11

[58] Field of Search ..... Plt./11, 12, 14, 18

*Primary Examiner*—Howard J. Locker

*Attorney, Agent, or Firm*—Klarquist, Sparkman, Campbell, Leigh and Whinston

[57] ABSTRACT

A hybrid tea rose plant having novel white flower edged in pink, very long exhibition-style bud and large open flower, long cutting stems making it an ideal garden cut rose, good vase life, and moderate fragrance.

1 Drawing Sheet

The present invention relates to a new and distinct variety of rose plant of the hybrid tea class which was originated by me by crossing the variety Jacolite, U.S. Plant Pat. No. 4,167, with the variety First Prize, U.S. Plant Pat. No. 2,774.

The primary objective of this breeding was to produce a new rose variety having the long stems and good flower production of Jacolite combined with the very large flower of First Prize. The objective was substantially achieved along with other desirable improvements as evidenced by the following unique combination of characteristics which are outstanding in the new variety and which distinguish it from its parents, as well as from all other varieties of which I am aware:

1. Novel white flower edged in pink.
2. Very long exhibition-style bud and large, open flower.
3. Long cutting stems making it an ideal garden cut rose.
4. Good vase life.
5. Moderate fragrance.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with the Royal Horticultural Society (London) Colour Chart, except where ordinary dictionary significance of color is indicated.

Parentage:

*Seed parent.*—Jacolite, U.S. Plant Pat. No. 4,167.

*Pollen parent.*—First Prize, U.S. Plant Pat. No. 2,774.

Classification:

*Botanical.*—*Rosa hybrida.*

*Commercial.*—Hybrid tea.

FLOWER

Observations made from specimens grown in a garden in Somis, Calif. in September, 1990.

Blooming habit: Recurrent.

Bud:

*Size.*—1¾ to 2 inches when the petals start to unfurl.

*Form.*—Long, pointed ovoid.

*Color.*—When sepals first divide, bud color is White group 155D, edged with Red Group 52C. When half blown, the upper sides of the petals are White Group 155D with a hint of pink on the petal edges; and the lower sides of the petals are White Group 155D with a hint of pink on the petal edges.

*Sepals.*—Color: Green Group 137A overlaid with reddish color. Surface texture: Covered with fine hairs. There are three normally to heavily appendaged sepals. There are two unappendaged sepals with hairy edges.

*Receptacle.*—Color: Green Group 143A often with a reddish cast. Shape: Funnel. Size: Large (½"×⅜"). Surface: Smooth.

*Peduncle.*—Length: Medium (3"). Surface: Glandular. Color: Bronzy. Strength: Stiff, erect, heavy.

Bloom:

*Size.*—Very large. Average open size is 5½ to 6 inches.

*Borne.*—Singly.

*Stems.*—Long (18 to 22"), strong.

*Form.*—When first open: High center. Permanence: Retains form to the end, outer petals curl back with some quilling.

*Petalage.*—Number of petals under normal conditions: many.

*Color.*—The upper side of the petals is White Group 155D with a hint of pink on the petal edges (Red Group 52D). The reverse side of the petals is White Group 155D with a hint of pink on the petal edges (Red Group 52D). The base of each petal has a light yellow half moon (Yellow Group 3D) (¼"×¼") at the point of attachment. The major color on the upper side is White Group 155D.

*Variegations.*—None.

*Discoloration.*—No change in the general tonality at the end of the first day. At the end of the third day, pink fades as flower opens fully to almost totally white.

*Fragrance.*—Moderate.

Petals:

*Texture.*—Thick, leathery.

*Shape.*—Round.

*Form.*—Tips slightly recurved, edges slightly quilled.

*Arrangement.*—Imbricated, with few petaloids in the center.

*Persistence.*—Hang on and dry.

*Lastingness.*—On the plant: Long (5 to 7 days). As a cut flower: Long (about 7 days).

Reproductive parts:

*Anthers.*—Size: Large. Quantity: Many. Color: Yellow. Arrangement: Regular around styles.

*Filaments.*—Color: Reddish.

*Pollen.*—Color: Lemon yellow.

*Styles.*—Color: Reddish.

*Stigmas.*—Color: Greenish white.

Form: Bush.

Growth: Vigorous, upright, branching.

Foliage:

*Number of leaflets on normal mid-stem leaves.*—5.

*Size.*—Large (6"×4").

*Quantity.*—Abundant.

*Color.*—New foliage: Bronze. Old foliage: Dark green.

Leaflets:

*Shape.*—Broadly oval.

*Texture.*—Upper side: Leathery.

*Edge.*—Serrated.

*Serration.*—Single, small.

*Petiole rachis.*—Color: Reddish.

*Petiole underside.*—Smooth.

*Stipules.*—Long (1 to 1⅛"), bearded.

*Disease resistance.*—Susceptible to mildew; resistant to rust under normal growing conditions at Somis, Calif.

Wood:

*New wood.*—Color: Reddish. Bark: Smooth.

*Old wood.*—Color: Green. Bark: Smooth.

Prickles:

*Quantity.*—Many on main canes from base and on laterals from main canes.

*Form.*—Long, hooked downward.

*Color when young.*—Red.

Small prickles:

*Quantity.*—On main stalks: None. On laterals: None.

I claim:

1. A new and distinct variety of rose plant of the hybrid tea class, substantially as herein shown and described, characterized particularly as to novelty by the unique combination of its novel white flower color that is edged in pink, its long bud and large, well-formed open flower that make it a good exhibition rose, its long cutting stems and good vase life that make it a good garden cut rose, and its pleasant fragrance.

* * * * *

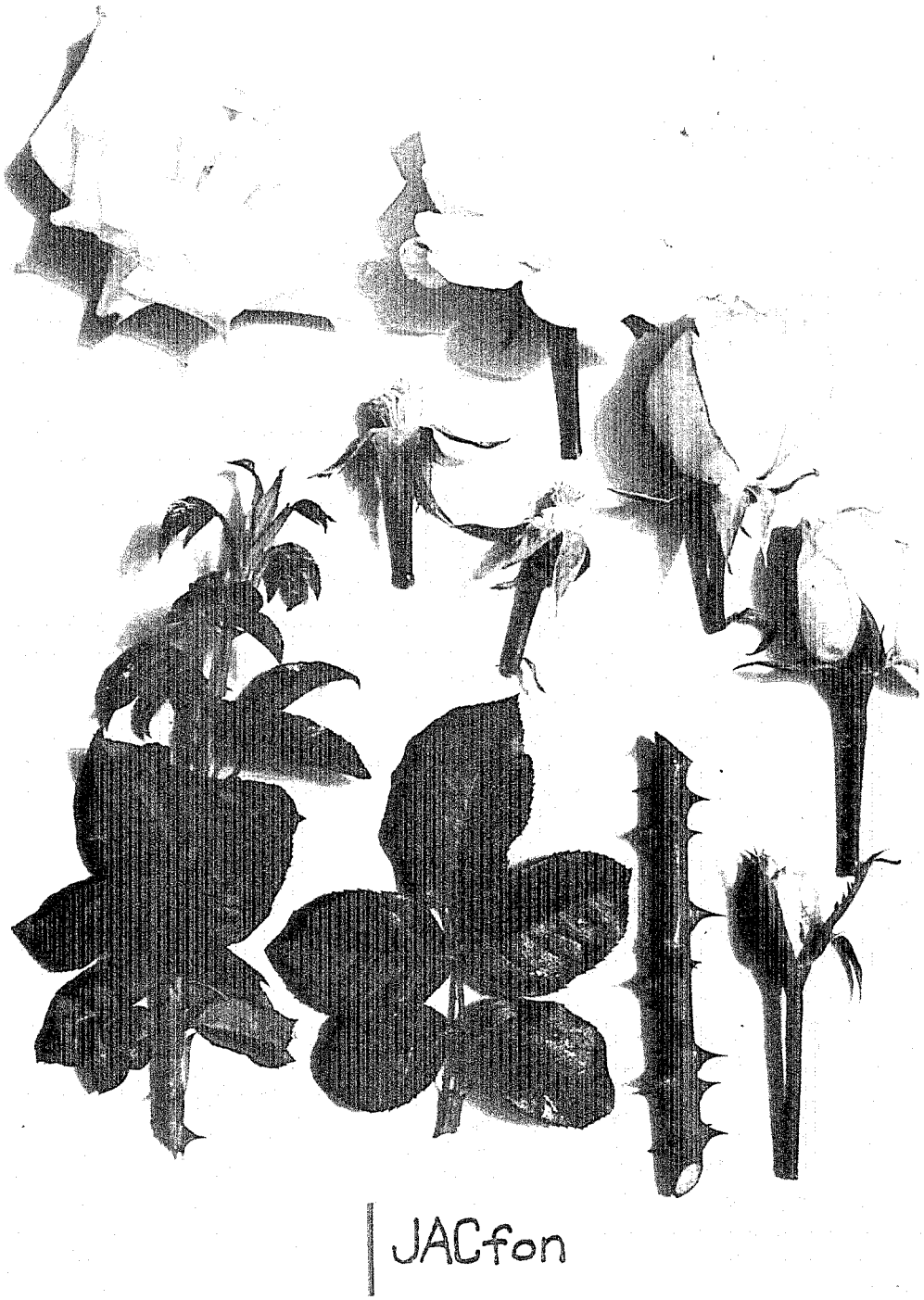
JACfon